US012324712B2

(12) United States Patent
Van Den Houdt et al.

(10) Patent No.: US 12,324,712 B2
(45) Date of Patent: Jun. 10, 2025

(54) DECONTAMINATION DEVICE AND METHOD FOR MEDICAL INSTRUMENTS

(71) Applicant: Log10 B.V., Eindhoven (NL)

(72) Inventors: Andreas Adrianus Lambertus Van Den Houdt, Eindhoven (NL); Franciscus Maria Verhoeven, Eindhoven (NL); Paul Herman Maria Pessers, Eindhoven (NL)

(73) Assignee: LOG10 B.V., Eindhoven (NL)

( * ) Notice: Subject to any disclaimer, the term of this patent is extended or adjusted under 35 U.S.C. 154(b) by 976 days.

(21) Appl. No.: 17/221,963

(22) Filed: Apr. 5, 2021

(65) Prior Publication Data

US 2021/0236236 A1 Aug. 5, 2021

Related U.S. Application Data

(63) Continuation-in-part of application No. 15/575,967, filed as application No. PCT/NL2016/050360 on May 20, 2016, now abandoned.

(30) Foreign Application Priority Data

May 21, 2015 (NL) ..................................... 2014837

(51) Int. Cl.
*A61B 90/70* (2016.01)
*A61B 1/12* (2006.01)
(Continued)

(52) U.S. Cl.
CPC .............. *A61B 90/70* (2016.02); *A61B 1/123* (2013.01); *A61L 2/183* (2013.01); *A61L 2/202* (2013.01);
(Continued)

(58) Field of Classification Search
CPC ......... A61B 90/70; A61B 1/123; A61L 2/183; A61L 2/202; A61L 9/14; A61L 2/186;
(Continued)

(56) References Cited

U.S. PATENT DOCUMENTS

| 2,428,481 | A | 10/1947 | Wagner |
| 4,014,158 | A | 3/1977 | Rausing |

(Continued)

FOREIGN PATENT DOCUMENTS

| CA | 987579 A | 4/1976 |
| CN | 1222086 A | 7/1999 |

(Continued)

OTHER PUBLICATIONS

Notice of Reasons for Rejection dated Oct. 6, 2020 issued in corresponding Japanese Patent Application No. 2018-247221 with English translation (11 pgs.).

(Continued)

*Primary Examiner* — Sean E Conley
(74) *Attorney, Agent, or Firm* — Pillsbury Winthrop Shaw Pittman, LLP

(57) ABSTRACT

The invention relates to a decontamination device for medical instruments and a method for decontaminating medical instruments. The device includes a reception unit arranged for receiving a to be treated medical instrument. The device further includes a washing unit arranged for washing and/or drying the instrument. The device includes a disinfection unit arranged for disinfecting the instrument. The device includes a delivery unit arranged for presenting the disinfected instrument to be taken out of the decontamination device.

20 Claims, 3 Drawing Sheets

(51) Int. Cl.
*A61L 2/18* (2006.01)
*A61L 2/20* (2006.01)
*A61L 9/14* (2006.01)
*A61L 2/24* (2006.01)

(52) U.S. Cl.
CPC .............. *A61L 9/14* (2013.01); *A61L 2/186* (2013.01); *A61L 2/24* (2013.01); *A61L 2202/182* (2013.01); *A61L 2202/24* (2013.01)

(58) Field of Classification Search
CPC ... A61L 2/24; A61L 2202/182; A61L 2202/24
See application file for complete search history.

(56) References Cited

U.S. PATENT DOCUMENTS

| | | | |
|---|---|---|---|
| 5,464,580 | A | 11/1995 | Popescu et al. |
| 5,571,488 | A * | 11/1996 | Beerstecher ............. A61L 2/24 134/94.1 |
| 5,607,612 | A * | 3/1997 | Held .................... H05B 6/6494 219/762 |
| 2002/0153021 | A1 | 10/2002 | Audet |
| 2004/0062693 | A1 | 4/2004 | Lin et al. |
| 2004/0250837 | A1 | 12/2004 | Watson |

FOREIGN PATENT DOCUMENTS

| | | |
|---|---|---|
| CN | 1955073 A | 5/2007 |
| CN | 203635580 U | 6/2014 |
| DE | 2339517 A1 | 2/1974 |
| EP | 0685399 A1 | 12/1995 |
| EP | 1444992 B1 | 12/2005 |
| EP | 1787662 A1 | 5/2007 |
| EP | 1787731 A2 | 5/2007 |
| EP | 2292340 A1 | 3/2011 |
| JP | 61-14128 A | 6/1986 |
| JP | 05-15952 U | 3/1993 |
| JP | H08-164190 A | 6/1996 |
| JP | 2004-24926 A | 1/2004 |
| JP | 3574697 B2 | 7/2004 |
| JP | 2010-537753 A | 12/2010 |
| WO | 2005070205 A1 | 8/2005 |
| WO | 2007000639 A1 | 1/2007 |
| WO | 2007/045943 A1 | 4/2007 |
| WO | 2009030599 A1 | 3/2009 |

OTHER PUBLICATIONS

Second Office Action dated Jun. 11, 2020 issued in corresponding Chinese Patent Application No. 201680039669.9 with English translation (12 pgs.).
International Search Report PCT/NL2016/050360 dated Jan. 2, 2017.
Notice of Reasons for Refusal dated Mar. 3, 2020 issued in corresponding Japanese Patent Application No. 2018-513261 with English translation (10 pgs.).
Communication pursuant to Rule 164(2)(b) and Article 94(3) EPC, dated Mar. 19, 2019 issued in corresponding European Patent Application No. 16742020.7.
International Preliminary Report on Patentability and Written Opinion of the International Searching Authority dated Nov. 21, 2017 issued in corresponding International Patent Application No. PCT/NL2016/050360.
Communication pursuant to Article 94(3) EPC dated Nov. 12, 2024, issued in corresponding European Patent Application No. 16 742 020.7 (10 pgs.).
English translation of Office Action dated Feb. 13, 2025, issued in corresponding Chinese Patent Application No. 201680039669.9 (7 pgs.).
Guidelines for Hospital Disinfection Management and Overall Technology, edited by Wei Qiuhua, Military Medical Science Publishing House, p. 22, Apr. 2015, 1st Edition, 1st Printing with English translation (9 pgs.)—corresponds to Exhibit 1: Hospital Sterilization Management and Overall Technical Guidelines, as noted in English Translation of CN Office Action dated Feb. 13, 2025.

* cited by examiner

DECONTAMINATION DEVICE AND METHOD FOR MEDICAL INSTRUMENTS

CROSS REFERENCE TO RELATED APPLICATIONS

This application claims priority to U.S. application Ser. No. 15/575,967, filed Nov. 21, 2017, which is the U.S. National Phase of PCT/NL2016/050360 filed May 20, 2016, which claims priority to Netherlands Patent Application No. 2014837, filed May 21, 2015, the contents of all of which are incorporated herein by reference in their entireties.

FIELD OF THE INVENTION

The present invention relates to a decontamination device and method for medical instruments. More in particular, the present invention relates to a device for disinfecting and/or sterilizing medical instruments, such as dental instruments.

BACKGROUND TO THE INVENTION

Medical instruments that have been used in a medical procedure are often contaminated with body fluids, tissue, micro-organisms or the like. The contaminated instruments can only be used again after decontamination to avoid cross-contamination from one patient to another. Decontamination can include one or more of rinsing, washing, drying, disinfecting and sterilizing. Normally these steps are carried out by trained personnel and/or dedicated machinery.

SUMMARY OF THE INVENTION

It is an object of the invention to provide a decontamination device and a method that render the task of decontaminating a medical instrument less cumbersome, less time-consuming and/or less expensive.

Thereto according to the invention is provided a decontamination device for medical instruments. The device includes a reception unit arranged for receiving a to be treated medical instrument. The device includes a washing unit arranged for washing and/or drying the instrument. The device includes a disinfection unit arranged for disinfecting the instrument, e.g. the washed and/or dried instrument. The device includes a delivery unit arranged for presenting the disinfected instrument to be taken out of the decontamination device.

This provides the advantage that all functionality for cleaning a medical instrument is present within one single device. Thus, cleaning the medical instrument is easier, faster, requires less handling time and requires no human interaction during the decontamination process.

Optionally, the decontamination device includes a wrapping unit arranged for providing the disinfected instrument in a holder. The instrument in the holder can be hermetically sealed from ambient air. The delivery unit can then be arranged for presenting the, e.g. hermetically sealed, holder including the decontaminated instrument to be taken out of the decontamination device. This provides the advantage that the instrument, once disinfected, is provided in the holder protected against contamination. The holder can then be opened prior to use of the disinfected instrument. Cleanliness of the instrument can hence be guaranteed to a great extent.

Optionally, the decontamination device includes a control unit arranged for controlling the washing unit, the disinfection unit and optionally the wrapping unit, for automatically washing and/or drying and disinfecting the instrument and optionally automatically providing the disinfected instrument in the holder hermetically sealed from ambient air. Hence the entire cleaning of the instrument can be automated. Thus, an operator only needs to enter the to be treated instrument into the reception unit and to retrieve the disinfected instrument from the delivery unit. No manual handling of the partially decontaminated instrument is required.

Optionally, the reception unit and the delivery unit are one and the same. This provides the advantage that the disinfected instrument can be retrieved at the same unit where it was entered into the device. This may also allow for designing the device to be compact. It will be appreciated that it is possible that the washing unit, the disinfecting unit and optionally the wrapping unit share the same space.

Optionally, at least the reception unit, the disinfection unit, and the delivery unit are consecutive stations within the device. This provides the advantage that the device can be designed as a feed-though device. This allows a part of the device that comes into contact with contaminated instruments to be physically separated, or at least at a distance, from a part of the device that presents the decontaminated instruments. Hence, cross-contamination may be prevented. It is for instance possible that the reception unit is positioned in a first room and the delivery unit is in a different second room, the decontamination device passing through a divider, such as a wall, separating the first and second rooms. Hence it is possible to provide a physical barrier between a contaminated side of the decontamination device and a decontaminated side of the decontamination device.

Optionally, the washing unit is a consecutive station within the device, e.g. located between the reception unit and the disinfection unit. Hence, disinfecting can be performed after washing. Optionally, the wrapping unit is a consecutive station within the device, e.g. located between the disinfection unit and the delivery unit.

Optionally, the disinfection unit is arranged for sterilizing the instrument. It will be appreciated that depending on the circumstances it may suffice to disinfect an instrument, wherein a large proportion of microorganisms is killed, although not all microorganisms are necessarily killed. In other cases it is preferred to sterilize the instrument, wherein substantially all microorganisms are killed.

Optionally, the disinfection unit is arranged for treating the instrument with a disinfectant, such as ozone. Optionally the disinfection unit is arranged for treating the instrument with a gaseous disinfectant, such as gaseous ozone. The ozone can be used for disinfection or sterilizing the instrument.

Optionally, the washing unit is arranged for washing debris off the instrument. Hence, debris, such as tissue, can be rinsed off the instrument. Washing off debris can precede a further washing step.

Optionally, the washing unit includes at least one nozzle to spray a jet or mist of a cleaning fluid directly onto the instrument. Hence, the instrument can be washed effectively. The cleaning fluid can be water, a detergent or a combination thereof. Optionally, the decontamination device, e.g. the washing unit, is arranged for washing the instrument using a liquid, such as water, containing a disinfectant, such as ozone. Washing with a liquid containing the disinfectant, e.g. ozone, can already provide a level of disinfection. Washing with a liquid containing the disinfectant can follow an earlier washing step such as washing off debris and/or washing with water and/or detergent.

Optionally, the washing unit includes at least one nozzle to spray a jet or mist of a drying gas directly onto the instrument. Hence drying of the washed instrument can be performed effectively.

Optionally, the decontamination device, e.g. the washing unit, is arranged for drying the instrument using a gas containing a disinfectant, such as ozone. Drying with a gas containing the disinfectant, e.g. ozone, can already provide a level of disinfection. It will be appreciated that using ozone provides the advantage that it can easily be used both as component in the washing liquid, and in gaseous form, e.g. for drying and in the disinfection unit. When the washing unit is arranged for drying and located between the reception unit and the disinfection unit, disinfecting can be performed after washing and drying. More in general disinfecting can be performed after drying.

Optionally, the wrapping unit is arranged for packaging the disinfected instrument in a hermetically sealed holder. The hermetically sealed holder can be a bag, a box, a container, or the like. This provides the advantage that the instrument, once disinfected, is protected against contamination microbial growth in the hermetically sealed holder. The holder can then be opened prior to use of the disinfected instrument. Cleanliness of the instrument can hence be guaranteed to a great extent. An indication of an expiry date can be placed on the hermetically sealed holder.

Optionally, the decontamination device is arranged for holding the instrument in a cassette. Hence, the instrument can be treated in the device while positioned in the cassette. Using the cassette can greatly improve the ease of handling different instruments. It is possible that the cassette is arranged for holding a plurality of instruments. It is also possible that the cassette is arranged for holding a specific instrument or a specific type of instrument. It is also possible that the cassette is arranged for holding one or more of different types of instruments.

Optionally, the reception unit is arranged for receiving the to be treated medical instrument loaded in a cassette. Hence, the instrument can be loaded in the cassette and the cassette can be inserted into the reception unit. Optionally, the washing unit is arranged for washing and/or drying the instrument in the cassette. Hence, the instrument need not be taken out of the cassette for being washed and/or dried. This greatly simplifies handling of the instrument inside the washing unit. Optionally, the disinfection unit is arranged for disinfecting the instrument in the cassette. Hence, the instrument need not be taken out of the cassette for being disinfected or sterilized. This greatly simplifies handling of the instrument inside the disinfection unit. Optionally, the wrapping unit is arranged for hermetically sealing the cassette containing the disinfected instrument. Thus the cassette can also serve as the holder. Optionally, the delivery unit is arranged for presenting the cassette containing the disinfected instrument to be taken out of the decontamination device. Hence, the disinfected instrument can be taken out of the decontamination device while remaining in the cassette. This greatly reduces the risk of the instrument becoming contaminated while or after taking the disinfected instrument out of the delivery unit.

Optionally, the cassette includes a first portion and a second portion that can be closed against each other for enclosing the instrument. The first portion can e.g. be a tray and the second portion can e.g. be a lid. This provides the advantage that the instrument, or a plurality of instruments, can easily be loaded into the cassette. The cassette can include one or more openings for allowing washing liquids, drying gases and/or disinfectants to pass into and/or out of the cassette.

Optionally, the wrapping unit is arranged for hermetically closing the first portion against the second portion. Thereto the wrapping unit can e.g. by provide a seal, such as a self-adhesive ribbon or glue, at the interface of the first and second portions. Hence the cassette can easily be hermetically closed. The wrapping unit can also be arranged for hermetically closing the one or more openings of the cassette.

The cassette can be reusable. It is also possible that the cassette is a disposable, intended for single use.

Optionally, the decontamination device includes a transportation unit arranged for transporting the instrument and/or the cassette from the reception unit to the disinfection unit, possibly via the washing unit. Optionally, the transportation unit is arranged for transporting the instrument and/or the cassette from the disinfection unit to the delivery unit, possibly via the wrapping unit. It will be appreciated that the transportation unit may include one or more transportation sections for transporting the instrument and/or cassette from one unit to another.

Optionally the cassette has one or more interface locations for interfacing with the transportation unit.

Optionally, the decontamination device includes a labelling unit arranged for providing the instrument and/or the cassette with a label representative of the performed decontamination. The label can e.g. be a sticker or can be printed onto the instrument and/or the cassette. Hence it is possible to determine the decontamination performed on the instrument from the label. The label can include information on the performed decontamination, e.g. a code representative of performed process steps. The label can also include information representative of a location in a database where information on the performed decontamination is stored. The label can include information representative of a date and time of decontamination.

Optionally, the instrument is a dental instrument. The dental instruments can e.g. be scalpels, syringes, scopes, mirrors, drills, burs, discs, handpieces, excavators, turbines, files, reemers, (plastic) re-usables, disposables, prosthetics, implants, 3D printed implants, inserts, measuring devices, spreaders etc.

Optionally, the decontamination device is in accordance with norm EN ISO 15883-4 for washers-disinfectors. Optionally, the decontamination device is in accordance with norm EN ISO 14937 for sterilization of health care products. Optionally, the decontamination device is simultaneously in compliance with both norms.

Optionally, the disinfecting unit is arranged for providing a sterilizing agent including recombined ionized humidified air to the instrument for sterilizing the instrument. The recombined ionized humidified air can be obtained by treating air with a plasma device, e.g. feeding an air stream through a plasma source, and allowing the ionized air to at least partially recombine. The air can be humidified prior to feeding the air to the plasma source. Herein "air" refers to ambient air or air-like gas mixtures, such as a mixture of nitrogen and oxygen gas, possibly with further additions such as carbon dioxide gas. Optionally, the instrument is cooled prior to sterilization. This allows condensing of the sterilizing agent onto the instrument. Thus, efficient use is made of the sterilizing agent for sterilizing the instrument. Thereto, the temperature of the medical instrument, the temperature of disinfecting unit and the humidity of the sterilizing agent can be chosen appropriately. The condensing of the sterilizing agent onto the instrument has a beneficial effect on the effectivity of the sterilizing. Without wishing to be bound to any theory, it is believed that the condensate allows for proper covering of the entire surface of the instrument with sterilizing agent, as well as providing a synergistic effect between the active ingredients of the sterilizing agent with water in the condensate. Optionally, the sterilizing is performed at or below ambient pressure. The sterilizing can e.g. be performed at about 800-1050 mbar. The plasma source can be an ambient pressure plasma source. The ambient pressure plasma source can e.g. be operated at a pressure of 800-1200 mbar.

The invention also relates to a system including a decontamination device as described above and at least one cassette arranged for holding the instrument. Optionally, the system includes a plurality of cassettes. It is possible that the system includes cassettes of a first type and cassettes of a second type. The cassettes of the fist type may be arranged for receiving instruments of a first type. The cassettes of the second type may be arranged for receiving instruments of a different second type. It is also possible that the cassettes of the first type are arranged for undergoing a first decontamination cycle and the cassettes of the second type are arranged for undergoing a different second decontamination cycle.

The cassettes of the first type may differ from the cassettes of the second type in one or more mechanical features. The cassettes of the first and the second type may differ in a marker present on or in the cassette. The marker can e.g. be a bar-code, QR-code, RFID device, NFID device, color, or the like. The decontamination device can be arranged to recognize the marker of the cassette and to perform a decontamination cycle according to the identified marker.

The invention also relates to a method for decontaminating a medical instrument using a decontamination device. The method includes receiving a to be treated medical instrument in a reception unit. The method includes washing and/or drying the instrument in a washing unit. The method includes disinfecting the instrument in a disinfection unit. The method includes presenting the disinfected instrument to be taken out of the decontamination device in a delivery unit.

Optionally, the method includes providing the disinfected instrument in a holder, e.g. hermetically sealed from ambient air, by a wrapping unit. The step of presenting then includes presenting the, e.g. hermetically sealed, holder including the disinfected instrument to be taken out of the delivery unit.

According to an aspect a method is provided for decontaminating a medical instrument using a decontamination device, the method including: loading a to be treated medical instrument loaded into a cassette; loading the cassette into the decontamination device; washing and/or drying the instrument in the decontamination device; disinfecting and/or sterilizing the instrument in the decontamination device; hermetically sealing the cassette containing the disinfected and/or sterilized instrument in the decontamination device; and taking the cassette containing the disinfected and/or sterilized instrument out of the decontamination device. The steps of washing, disinfecting and drying can be performed in this order. The steps of washing, drying and sterilizing can be performed in this order. The steps of washing, disinfecting, drying and sterilizing can be performed in this order.

According to an aspect a method is provided for decontaminating a medical instrument using a decontamination device, the method including the following steps in this order: loading a to be treated medical instrument loaded into a cassette; loading the cassette into the decontamination device; washing the instrument in the decontamination device; disinfecting the instrument in the decontamination device; drying the instrument in the decontamination device; sterilizing the instrument in the decontamination device; hermetically sealing the cassette containing the disinfected and/or sterilized instrument in the decontamination device; and taking the cassette containing the disinfected and/or sterilized instrument out of the decontamination device.

According to an aspect a method is provided for decontaminating a medical instrument using a decontamination device, the method including in a first cycle rinsing the instrument; in a second cycle washing the instrument; in a third cycle disinfecting the instrument; in a fourth cycle drying the instrument; and optionally in a fifth cycle sterilizing the instrument.

According to an aspect a method is provided for decontaminating a medical instrument using a decontamination device, the method including the following steps in this order: loading a to be treated medical instrument loaded into a cassette; loading the cassette into the decontamination device; washing the instrument in the decontamination device; disinfecting the instrument in the decontamination device; drying the instrument in the decontamination device; cooling the instrument in the decontamination device; sterilizing the instrument in the decontamination device; hermetically sealing the cassette containing the disinfected and/or sterilized instrument in the decontamination device; and taking the cassette containing the disinfected and/or sterilized instrument out of the decontamination device.

Optionally, the decontamination device is a decontamination device as described above.

It will be appreciated that any of the features and options described in view of the device apply equally to the system and method, and vice versa. It will also be clear that any one or more of the above features and options can be combined.

BRIEF DESCRIPTION OF THE DRAWINGS

Embodiments of the present invention will now be described in detail with reference to the accompanying drawings in which.

DETAILED DESCRIPTION

Figure 1:
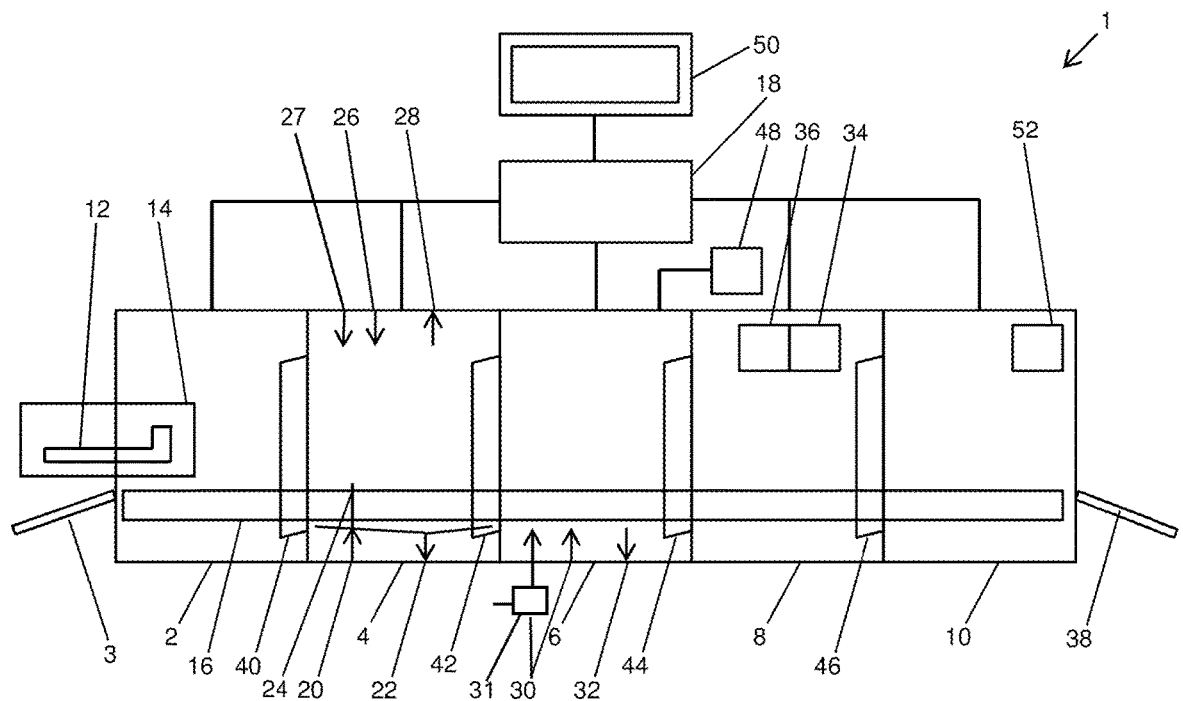
FIG. 1 is a schematic representation of a decontamination device.

FIG. 1 shows a schematic representation of a decontamination device 1 according to the invention. In this example the decontamination device includes a reception unit 2, a washing unit 4, a disinfection unit 6, a wrapping unit 8, and a delivery unit 10. The decontamination device 1 is arranged for decontaminating a medical instrument 12. Thereto, the medical instrument 12 to be treated is inserted into the reception unit 2, e.g. via a loading door 3 provided on the reception unit 2. In FIG. 1, the medical instrument 12 is loaded in a cassette 14. In this illustrative and non-limiting example, the reception unit 2 constitutes a chamber of the device 1. The loading door 3 can be opened for inserting the to be treated instrument 12, e.g. loaded in the cassette 14, therein.

In this example, the device 1 further includes a transportation unit 16 for transporting the cassette 14 from unit to unit as described below. Here, in accordance with an embodiment, the transportation unit 16 is a conveyor, such as a belt conveyor; however, such an example is not intended to be limiting. In accordance with embodiments, it is also possible that other transportation unit(s) is/are used, such as, but not limited to, conveyor arms, carts, tracks, chains, or the like, which may be used with a corresponding track, rails, wheels, or similar devices for moving cassette(s) or instrument(s) through the device 1. The transportation unit can be arranged to engage the cassette 14, in accordance with embodiments herein. The transportation unit 16 can be exposed in the reception unit 2. Here, the conveyor (16) is exposed such that the cassette 14 is placed on the conveyor (16) in the reception unit 2 when the door 3 is opened. It will be appreciated that it is also possible that the decontamination device 1 is arranged for handling the instrument 12 itself, i.e. not loaded in the cassette 14. Thereto, in embodiments, the transportation unit 16 may be arranged to engage the instrument 12 itself. Whether the transportation unit 16 is arranged to engage the cassette 14 and/or the to be treated instrument 12, in accordance with embodiments herein, the conveyor has securement devices, e.g. dedicated hooks, clamps, or receptacles, for example, for receiving an instrument 12 and/or the cassette 14. Also the additional exemplary embodiments—conveyor arms, carts, tracks, chains, or the like—may have securement devices (e.g. dedicated hooks, clamps or receptacles) for receiving an instrument 12 and/or the cassette 14. It will be appreciated that it is also possible that the decontamination device is arranged for being suitable to handle both instruments 12 loaded in cassettes 14 and instruments per se, i.e. not loaded in cassettes.

Figure 2:
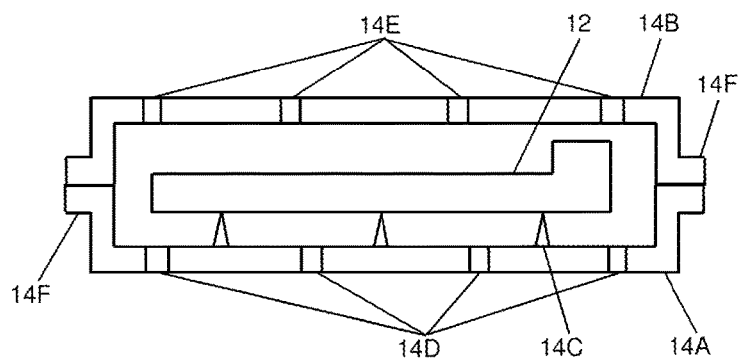
FIG. 2 is a schematic representation of a cassette.

In accordance with an embodiment herein, handling devices may be provided on a cassette 14 and/or instrument 12, such that the securement devices of the transportation unit 16 may correspondingly engage therewith (see, e.g., FIG. 2 and related description). Non-limiting examples of such handling devices include, but are not limited to, tabs, ridges, holes, and/or openings, for example.

The to be decontaminated instrument 12 is loaded into the cassette 14, in accordance with one embodiment. The cassette 14 is placed into the reception unit 2. In the reception unit 2 the cassette 14 is engaged by the transportation unit 16. For instance, the cassette is placed on the conveyor. Additionally and/or alternatively, [a cart or arm of] the transportation unit can have connection points and/or securement devices arranged for connecting to handling features, such as tabs or ridges, of the cassette 14.

The transportation unit 16 transports the cassette 14 from the reception unit 2 to the washing unit 4. In the washing unit 4 the instrument 12 can be washed. In this illustrative, non-limiting example, the washing unit 4 includes a chamber of the device 1; the chamber of the washing unit may be a same or separate chamber from the chamber of the reception unit 2. The washing unit 4 may include a bath for submerging the cassette 14 and/or instruments 12, in accordance with an embodiment. The washing unit 4 may include one or more ultrasonic transducers for ultrasonically cleaning the cassette and/or instruments, in accordance with one embodiment. The washing unit 4 may include a shower for rinsing and/or washing the cassette and/or instruments, in accordance with another embodiment. It will be appreciated that the decontamination device 1 may be operated according to different decontamination cycles. A control unit 18 is arranged for controlling operation of the respective units.

The washing unit 4 can be controlled to perform different washing cycles 102, 104. For example, as a first cycle the washing unit 4 may rinse the instrument 12 for washing off debris. Rinsing may e.g. be done using a liquid such as water. Thereto the washing unit 4 includes a washing liquid supply 20 and a washing liquid drain 22. The washing liquid supply can supply washing liquid to the to be treated instrument 12. The washing liquid can e.g. be supplied in the bath or via one or more shower heads or nozzles of the shower, in accordance with embodiments herein. The washing liquid supply may include one or more pumps for providing the washing liquid to the bath, shower, and/or nozzles. For example as a second cycle the washing unit 4 may wash the instrument 12 for at least partly washing of contaminants. Washing may e.g. be done using a liquid such as water and/or a detergent. In this example the washing unit 4 includes one or more nozzles 24 for spraying a jet or mist of the liquid directly onto the instrument 12. As shown in FIG. 1, the one or more nozzles 24 can be connected to the washing liquid supply 20. For example as a third cycle the washing unit may disinfect (see, e.g., step 106 in FIG. 5) the instrument 12 using a liquid, such as water, containing a disinfectant such as ozone. It will be appreciated that the washing unit may use a warm or hot liquid. For example as a fourth cycle the washing unit 4 may dry (see, e.g., step 108 in FIG. 5) the instrument 12 using a gas. Thereto the washing unit 4 includes a drying gas supply 26 and a drying gas exhaust 28. The drying gas supply can e.g. include a heater and/or ventilator. In accordance with embodiments herein, drying gas may e.g. be air, such as HEPA filtered air; in an embodiment, the air may be HEPA filtered air of HEPA class H13 or better, such as H14, U15, U16 or U17. For example as a fifth cycle the washing unit 4 may cool (see, e.g., step 109 in FIG. 5) the instrument 12. Thereto the washing unit 4 may include a cooling gas supply 27, in accordance with an embodiment. The cooling gas supply 27 may include a gas displacer, such as a ventilator, and optionally a cooler. The cooling can be performed by blowing a stream of the cooling gas at the instruments 12. The cooling gas may e.g. have a temperature of about 0-30° C., in accordance with an embodiment, and, in another embodiment, a temperature such as about or at 5-15° C. For example as a sixth cycle the washing unit 4 may disinfect (see, e.g., step 112 in FIG. 5) the instrument 12 using a gas containing ozone. The control unit 18 controls the washing unit 4 for performing one of more of the first, second, third, fourth, fifth, or sixth cycle, the order of the cycles, the duration of the cycles, the temperatures used in the cycles, etc.

The transportation unit 16 transports the cassette 14 (and/or instrument 12) from the washing unit 4 to the disinfection unit 6. In this illustrative, non-limiting example, the disinfection unit 6 includes a chamber of the device 1; the chamber of the disinfection unit may be a same or separate chamber from the chamber(s) of the reception unit 2 and/or washing unit 4. The disinfection unit 6 is arranged for disinfecting (see, e.g., steps 106, 112 in FIG. 5) the instrument 12. The disinfection unit 6 can be controlled to perform different disinfection cycles. For example as a first cycle (e.g., step 106) the disinfection unit 6 may disinfect the instrument using a disinfectant, such as gaseous ozone. Thereto the disinfection unit includes a disinfectant supply 30 and a disinfectant drain 32. The disinfectant supply 30 may include one or more nozzles for providing the disinfectant to the to be treated instrument. The disinfectant supply may include one or more pumps for providing the disinfectant (from supply 30) to the nozzles. The disinfectant supply may include a sterilizing agent supply. For example as a second cycle (see, e.g., step 112 in FIG. 5) the disinfection unit 6 may sterilize the instrument using a disinfectant, such as gaseous ozone. It is also possible that the disinfection unit 6 only sterilizes the instruments 12, in an embodiment. The sterilizing agent for sterilizing the instruments 12 may include recombined ionized humidified air. It will be appreciated that other disinfectants may also be used such as steam, ethylene oxide gas, dry heat, hydrogen peroxide, peracetic acid, performic acid, phenolics, etc. It will be appreciated that the disinfection unit 6 may also include a plurality of disinfectant supplies 30 for supplying a plurality of different disinfectants, in accordance with an embodiment. This allows the user, or the control unit 18, to select one or more appropriate disinfectants for the decontamination cycle. The plurality of disinfectant supplies may e.g. include multiple reservoirs for the multiple disinfectants, ducting, valves, and/or pumps. It is for instance possible to first perform a disinfection cycle (e.g., step 106) using gaseous ozone, followed by a sterilization cycle (e.g., step 112) using steam. It is also possible, in an embodiment, that the sterilization cycle is performed using a plasma or a plasma afterglow, generated by a plasma source 31. The plasma source 31 can generate the recombined ionized humidified air. Thereto, the plasma source 31 may include an input port for feeding a humidified air stream into the plasma source, and the plasma source is configured to at least partly ionize the humidified air, wherein the at least partly ionized humidified air is at least partly recombined prior to hitting the instruments 12. Cooling the instruments 12 prior to sterilizing can be particularly beneficial in case of sterilizing with the recombined ionized humidified air. However, other combinations are also possible. The control unit 18 controls the disinfection unit 6 for performing one of more of the first or second cycles, the order of the cycles, the duration of the cycles, the temperatures used in the cycles, the concentrations of disinfectants used in the cycles etc.

The transportation unit 16 transports the cassette 14 (and/or instrument 12) from the disinfection unit 6 to the wrapping unit 8. In this illustrative, non-limiting example, the wrapping unit 8 is arranged for sealing 114 the cassette 14. In this example, the wrapping unit 8 includes a chamber of the device 1; the chamber of the wrapping unit may be a same or separate chamber from the chamber(s) of the reception unit 2, washing unit 4, and/or disinfection unit 6. The wrapping unit 8 can be controlled to perform different wrapping cycles. For example as a first cycle the wrapping unit 8 may seal the cassette 14 with a tamper proof seal, for example. The tamper proof seal e.g. needs to be broken to remove the disinfected instrument 12 from the cassette 14. The tamper proof seal thus provides a guarantee that the instrument 12 has not been touched or used since disinfection. Thereto the wrapping unit 8 includes a seal supply unit 34. The seal supply unit 34 may e.g. include a plurality of seals, such as self-adhesive stickers, tape or the like. The seal supply unit 34 may also include an applicator for applying the seal to the cassette, such as, for example, a known labeling device. For example as a second cycle the wrapping unit 8 may hermetically seal the cassette 14. Thereto the wrapping unit may e.g. apply self-adhesive labels, stickers, tape or the like over apertures of the cassette 14. The wrapping unit 8 may e.g. include an applicator arm moving self-adhesive labels, stickers, tape or the like from a dispenser to the cassette. The applicator arm can e.g. directly apply self-adhesive labels, stickers, tape or the like from a roll of backing material onto the cassette. The arm can e.g. include a rolling mechanism for rolling off the backing material around a bend such as to partially free the self-adhesive labels, stickers, tape or the like from the backing material and apply the self-adhesive labels, stickers, tape or the like to the cassette. For example as a third cycle the wrapping unit 8 may enclose the cassette 14, or the instrument 12 in case no cassette 14 is used, in a holder such as a bag, box, container or the like. Thereto the wrapping unit 8 may include a holder supply unit 36. The wrapping unit 8 may hermetically seal the holder after insertion of the cassette 14 or instrument 12. Thereto the wrapping unit 8 may provide a seal, such as a self-adhesive ribbon or glue, to the cassette. The applicator can include known means, such as rollers, squeegees or the like, for applying the seal to the cassette. The wrapping unit 8 may e.g. apply the seal to a separation seam between the tray and the lid of the cassette 14. The wrapping unit 8 may also apply the seal to any openings in the cassette 14. The control unit 18 controls the wrapping unit 8 for performing one of more of the first, second or third cycles, the order of the cycles, etc.

The transportation unit 16 transports the cassette 14 from the wrapping unit 8 to the delivery unit 10. In this example, the delivery unit 10 includes a chamber of the device 1; the chamber of the delivery unit may be a same or separate chamber from the aforementioned chamber(s) of the wrapping unit, disinfection unit, etc. The delivery unit is arranged for presenting the disinfected instrument 12, here in the cassette 14, to be taken out (see, e.g., step 116 in FIG. 5) of the decontamination device 1. Thereto the delivery unit 10 may include an unloading door 38. The unloading door 38 may be positioned as part of the delivery unit 10 to allow taking of the instrument 12 and/or cassette 14 from the transportation unit 16. The transportation unit 16 can be exposed in the delivery unit 10. Here, in accordance with an embodiment, the conveyor is exposed such that the cassette 14 may be taken from the conveyor in the delivery unit 10 when the door 38 is opened. The control unit 18 controls the delivery unit 10, e.g. for locking the unloading door 38 for preventing unauthorized opening at unwanted, e.g. hazardous, moments. It will be appreciated that the decontamination device uses disinfectants, possibly in gaseous form. The loading door 3 and unloading door 38 therefore may require lock-down during application of such disinfectant. A controllable lock, such as an electrically actuatable lock, at the loading door 3 and/or unloading door 38 may thereto be included. It is also possible that the decontamination device includes one or more internal doors such as doors 40, 42, 44, 46 between the reception unit 2 and the washing unit 4, the washing unit 4 and the disinfection unit 6, the disinfection unit 6 and the wrapping unit 8, and the wrapping unit and the delivery unit 10, respectively. Lock-down of the internal doors 40, 42, 44, 46 can be controlled by the control unit 18, e.g. using controllable locks. It is also possible that the decontamination device 1 includes a pump device 48 for maintaining the decontamination device 1, e.g. the disinfection unit 6, at an underpressure in order to avoid egress of gaseous disinfectants.

As can be seen from FIG. 1, in this example the reception unit 2, especially the loading door 3 is physically separated from the delivery unit 10, especially the unloading door 38. There is a nonzero distance between the loading door 3 and the unloading door 38. Thus it is easy to keep contaminated instruments 12 away from decontaminated instruments 12. It is possible that the loading door 3 is in a first room and the unloading door 38 is in a different second room. In that case the decontamination device 1 extends through a wall between the first and second rooms. Hence, the first room can be a contaminated room, while the second room is a decontaminated room.

The decontamination device 1 performs the decontamination cycle under control of the control unit 18. The decontamination cycle can be selected and/or configured using user interface 50. The user interface may include one or more buttons, controls, a display, and/or a touchscreen. It will be appreciated that the control unit 18 controls the reception unit 2, the washing unit 4, the disinfection unit 6, the wrapping unit 8 and the delivery unit 10 for performing one of more of the respective cycles. It will be appreciated that it is also possible that the control unit 18 configures a decontamination cycle in which one or more of the washing unit 4, the disinfection unit 6 and the wrapping unit 8 does not perform a cycle.

The decontamination device 1 may be used for disinfecting and/or sterilizing contaminated instruments 12 according to methods utilizing various method steps and various units, such as 2, 4, 6, 8, 10, 16, of the decontamination device 1. The decontamination device 1 can e.g. be operated by loading a to be treated medical instrument 12 into a cassette 14 and loading the cassette 14 into the reception unit 2. From the reception unit, the cassette may be transported to the washing unit 4. In the washing unit 4 washing of the instruments 12 may be performed, such as rinsing and washing, e.g. ultrasonically washing the cassette 14 and/or instruments 12. Next, the cassette 14 and/or instruments 12 can be disinfected. Thereto the cassette 14 may be transported to the disinfection unit 6. Alternatively, the disinfecting can be performed in the washing unit 4. Next, the cassette 14 and/or instruments 12 can be dried. The drying can be performed in the washing unit 4 or in the disinfecting unit 6. Next, prior to sterilizing, the cassette 14 and/or instruments 12 may be cooled. The cooling can be performed in the washing unit 4 or in the disinfecting unit 6. Next, the cassette 14 and/or instruments 12 can be sterilized. The sterilizing can be performed in the disinfecting unit 6. Next, the cassette 14 can be transported to the wrapping unit 8. There the cassette 14 can be sealed.

Figure 5:
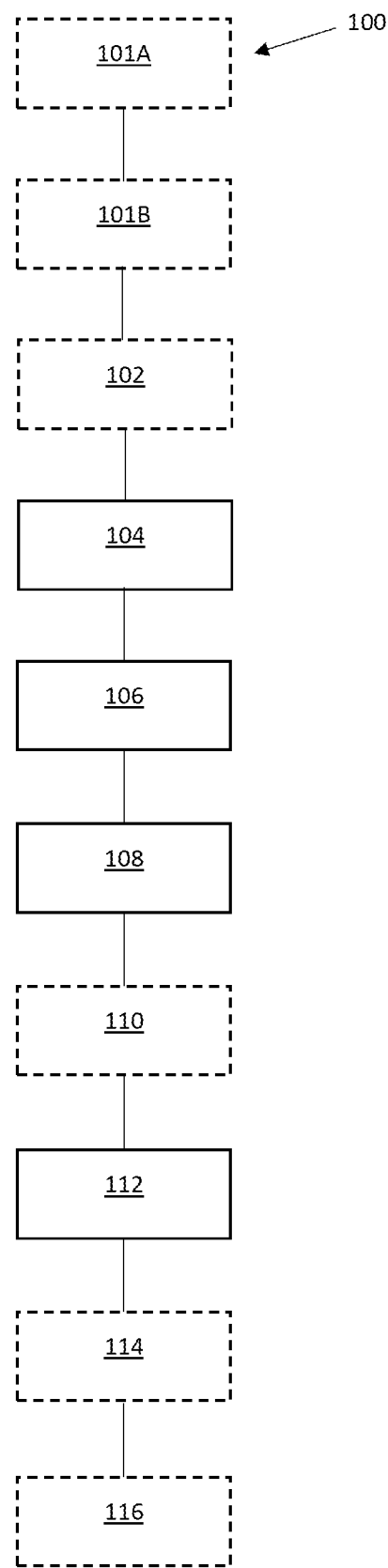
FIG. 5 is a schematic representation of a method.

FIG. 5 shows an exemplary method 100 for using the decontamination device 1. In accordance with an embodiment, the steps of the method are performed in the order indicated in FIG. 5. The method may also include the optional steps of loading 101A a to be treated medical instrument into a cassette, and loading 101B the cassette into the decontamination device, e.g., via the reception unit 2 (and loading door 3). In this example, the method may start with an optional preliminary step 102 of ultrasonically washing the cassette and/or instruments, e.g., using the washing unit 4. The ultrasonic washing at 102 may e.g. be performed at about 30-40° C. in accordance with embodiments, such as at about 37° C., in accordance with one exemplary embodiment. The ultrasonic washing step 102 may e.g. take about 10-300 seconds in accordance with one embodiment; about 100-200 seconds in accordance with another embodiment; and e.g. about 150-180 seconds, in accordance with yet exemplary embodiment. In a step 104 the cassette and/or instruments are washed, e.g. in the washing unit 4, e.g. as described above. The washing at 104 may e.g. be spray washing using nozzles, in accordance with an embodiment. The washing at 104 may e.g. be performed at a temperature of about 40-90° C. in accordance with an embodiment; at temperatures of about 60-80° C. in accordance with another embodiment; e.g. at a temperature of about 73° C., in accordance with yet another exemplary embodiment. The washing step at 104 may e.g. take about 10-300 seconds in an embodiment; about 60-180 seconds accordance with another embodiment; e.g. about 120 seconds, in accordance with yet another exemplary embodiment. In a step 106 the cassette and/or instruments are disinfected, e.g. as described above, using disinfection unit 6. The disinfecting at step 106 may e.g. be performed at a temperature of about 60-100° C., in accordance with an embodiment; at about 80-96° C., in accordance with another embodiment; or e.g. at about 93° C., in accordance with an exemplary embodiment. The disinfecting step at 106 may e.g. take about 10-300 seconds, in accordance with an embodiment; about 60-200 seconds, in accordance with another embodiment; e.g. about 150 seconds, in accordance with an exemplary embodiment. In an optional embodiment, the disinfecting step at 106 may include rinsing of the cassette 14 and/or instrument 12 to wash off debris. In a step 108 the cassette and/or instruments are dried, e.g. as described above. The drying at 108 may e.g. be performed at a temperature of about 60-100° C., in accordance with an embodiment; at about 80-96° C., in accordance with another embodiment; e.g. at about 82° C., in accordance with an exemplary embodiment. The drying step at 108 may e.g. take about 10-300 seconds, in accordance with one embodiment; about 60-240 seconds in accordance with another embodiment; e.g. about 225 seconds, in accordance with an exemplary embodiment. In an optional step 110 the cassette and/or instruments are cooled, e.g. as described above. The cooling at 110 may e.g. be performed at a temperature of about 0-30° C., in accordance with one embodiment; at about 5-15° C., in accordance with an exemplary embodiment. The cooling step at 110 may e.g. take about 10-300 seconds, in accordance with one embodiment; about 60-240 seconds, in accordance with an exemplary embodiment. In a step 112 the cassette and/or instruments are sterilized, e.g. as described above, using disinfection unit 6. The sterilizing at 112 may e.g. be performed using a plasma or a plasma afterglow, e.g. using the sterilizing agent including the recombined ionized humidified air, in accordance with an exemplary embodiment. The sterilizing step may e.g. take about 300-3000 seconds, in accordance with one embodiment; about 1500-2000 seconds, according to another embodiment; e.g. about 1800 seconds, in accordance with an exemplary embodiment. Alternatively, in step 112 the cassette and/or instruments are disinfected, e.g. as described above, e.g. using the disinfecting agent including the recombined ionized humidified air. The disinfecting at 112 may e.g. be performed using a plasma or a plasma afterglow, in accordance with an exemplary embodiment. The disinfecting step at 112 may e.g. take about 10-300 seconds, in accordance with one embodiment; about 30-180 seconds, according to another embodiment; about 60 seconds, in accordance with an exemplary embodiment. Finally the method may include one or more of the optional steps of hermetically sealing 114 or wrapping the cassette containing the disinfected and/or sterilized instrument using wrapping unit 8, and taking 116 the cassette containing the disinfected and/or sterilized instrument out of the decontamination device, via delivery unit 10.

In the example of FIG. 1 the decontamination device 1 includes an optional labelling unit 52, such as a sticker label applicator or printer. The labelling unit 52 is arranged for providing the instrument 12 and/or the cassette 14 with a label representative of the performed decontamination. The label can e.g. be a sticker or can be printed (via printer) onto the instrument 12 and/or the cassette 14. In an embodiment, the labelling unit 52 includes a roller, and/or a movable arm for taking a label or sticker (e.g., from a supply or roll of labels), to apply said label or sticker to instrument and/or cassette. Hence it is possible to determine the decontamination performed on the instrument from the label. The label can include information on the performed decontamination, e.g. a code representative of the performed decontamination cycle. The label can also include information representative of a location in a database where information on the performed decontamination cycle is stored. The label can include information representative of a date and time of the performed decontamination cycle.

FIG. 2 shows a schematic representation of a cassette 14. In this example the cassette includes a tray 14A and a lid 14B. In this example the tray 14A includes carriers 14C for carrying an instrument 12. In this example the tray 14A includes openings 14D for allowing washing liquids, drying gases and disinfectants to pass. In this example the lid 14B includes openings 1E for allowing washing liquids, drying gases and disinfectants to pass. Preferably the openings 14D, 14E are arranged such that they can be easily sealed by the wrapping unit 8, e.g. by applying a seal, such as a sticker, over the respective opening. Thereto, the openings may e.g. be positioned close to the interface between the tray 14A and the lid 14B. In FIG. 2 the cassette 14 includes handling points 14F arranged for being engaged by the transportation unit 16. As previously noted, examples of such handling points may include, but are not limited to, tabs, ridges, holes, and/or openings on the cassette 14 (and/or instrument). The transportation unit 16, e.g. a conveyor belt, cart, or arm of the transportation unit, may include securement or gripping features arranged to mesh with the handling points 14F, in accordance with an embodiment. Hence secure handling of the cassette can be obtained within the decontamination device 1 as the cassette/instrument is moved therethrough.

It will be appreciated that different types of cassettes 14 may be associated with the decontamination device 1. There may be cassettes 14 of a first type and cassettes 14 of a second type. The cassettes 14 of the fist type may be arranged for receiving instruments 12 of a first type. The cassettes 14 of the second type may be arranged for receiving instruments 12 of a different second type. Thereto the cassettes of the first and second types may include mutually different carriers 14C. It is possible that the exterior dimensions of the cassettes of the first and second type are the same. It is also possible that the exterior dimensions of the cassettes of the first and the second type are different. In the latter case preferably the handling points 14F of both types of cassettes are the same, so that the transportation unit 16 can handle both types of cassettes.

It is also possible that the cassettes 14 of the first type are arranged for undergoing a first decontamination cycle and the cassettes 14 of the second type are arranged for undergoing a different second decontamination cycle. Thereto the user may instruct the control unit 18 to perform the different decontamination cycles.

Figure 3:
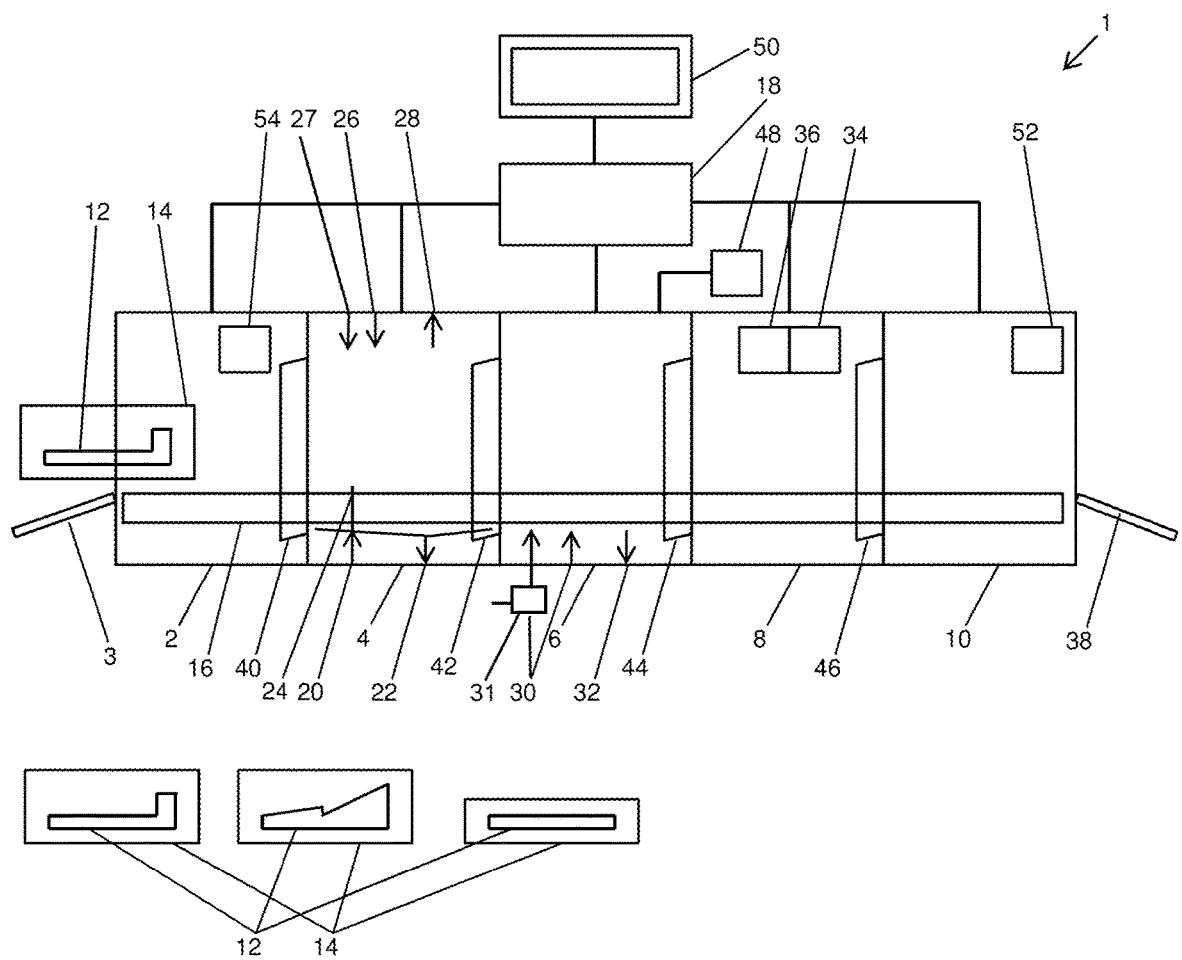
FIG. 3 is a schematic representation of a decontamination device.

FIG. 3 shows a schematic representation of a decontamination device 1 according to the invention. This decontamination device is similar to the decontamination device 1 shown in FIG. 1. In this example, the decontamination device 2 further includes a recognition unit 54. The recognition unit 54 is arranged for recognizing the different types of cassettes. It is possible that the control unit 18 stores a plurality of sets of instructions, each representative of a specific decontamination cycle. The control unit 18 may store a list including for each type of cassette an associated decontamination cycle. Upon recognizing the type of cassette, the decontamination device 2 can automatically select the associated decontamination cycle, and perform said cycle. Hence, medical instruments can easily be loaded into an appropriate cassette that has a decontamination cycle associated therewith that is suitable for the instrument at hand.

The different types of cassettes may differ in a marker present on or in the respective cassettes. The marker can e.g. be a mechanical indicator, a bar-code, a two-dimensional barcode, a QR-code, a Radio Frequency Identification (RFID) device, a Near Field Identification (NFID) device, a color of the cassette, a color of part of the cassette, a color code or the like. The recognition unit 54 decontamination device can be arranged to recognize the marker of the cassette and to perform a selected decontamination cycle according to the identified marker. The recognition unit may e.g. include a camera and/or a device for reading machine readable codes, such as a camera, mechanical feeler, barcode reader, QR-code reader, RFID reader, NFID reader or the like, in accordance with embodiments.

Figure 4:
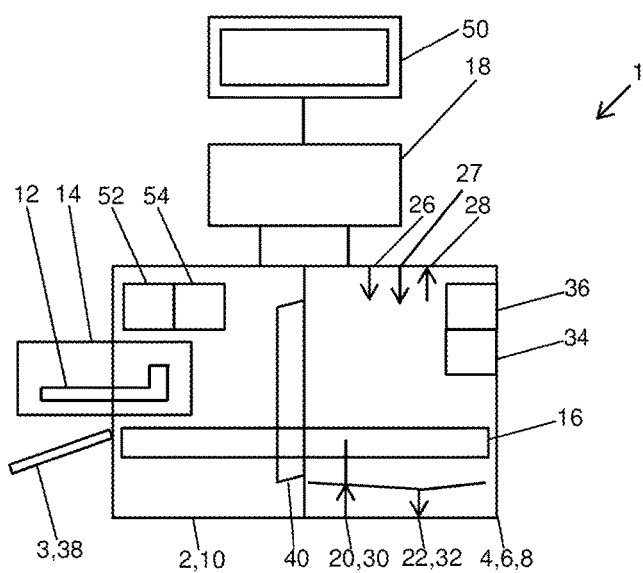
FIG. 4 is a schematic representation of a decontamination device.

FIG. 4 shows a schematic representation of a decontamination device 1 according to the invention. The functioning of this decontamination device 1 is similar to that of the device 1 described with respect to FIG. 1 and FIG. 3. In this example, the reception unit 2 and the delivery unit share the same space. In this example, one physical entity performs both the function of the reception unit 2 and the delivery unit 10. In this example the joint reception and delivery unit includes a single loading and unloading door. In this example, the washing unit 4, the disinfection unit 6 and the wrapping unit 8 share the same space. In this example one physical entity performs the functions of the washing unit 4, the disinfection unit 6 and the wrapping unit 10. It will be clear that the decontamination device may include an internal door 40. The decontamination device of the present example can for instance be embodied as a desk top or counter top device. The decontamination device may be embodied in a size according to general kitchen appliances, such as an oven or microwave oven. The dimensions of the decontamination device may be approximately 60 cm wide, 40 cm high and 50 cm deep. Hence, the decontamination device can easily be integrated into a medical work environment, such as a cupboard e.g. of a dental practice.

Herein, the invention is described with reference to specific examples of embodiments of the invention. It will, however, be evident that various modifications and changes may be made therein, without departing from the essence of the invention. For the purpose of clarity and a concise description features are described herein as part of the same or separate embodiments, however, alternative embodiments having combinations of all or some of the features described in these separate embodiments are also envisaged.

In the example of FIG. 1 the reception unit 2, the washing unit 4, the disinfection unit 6, the wrapping unit 8 and the delivery unit 10 are shown as physically separate units occupying different spaces. It will be appreciated that one or more of the reception unit 2, the washing unit 4, the disinfection unit 6, the wrapping unit 8 and the delivery unit 10 may also share the same space. It is for instance possible that the reception unit 2 occupies the same space as the washing unit 4, i.e. for instance the washing cycles being performed on the cassette 14 or instrument 12 on the same location where it was inserted into the decontamination device 1. It will be appreciated that the transportation unit 16 then need not transport the cassette 14 or instrument 12 from the reception unit 2 to the washing unit 4. Similarly, the washing unit 4 and the disinfection unit 6 can occupy the same space, the disinfection being performed on the cassette 14 or instrument 12 at the same location as the washing.

Similarly, the disinfection unit 6 and the wrapping unit 8 can occupy the same space, the wrapping being performed on the cassette 14 or instrument 12 at the same location as the disinfecting. Similarly, the wrapping unit 8 and the delivery unit 10 can occupy the same space, the presenting of the cassette 14 or instrument 12 being performed at the same location as the wrapping.

In the examples mention is made of cassettes of a first type and cassettes of a second type. It will be appreciated that it is possible that the decontamination device has a plurality of types of cassettes associated therewith.

It will be appreciated that it is also possible that the decontamination device does not include all of the reception unit 2, the washing unit 4, the disinfection unit 6, the wrapping unit 8 and the delivery unit 10. Embodiments can be envisaged in which for example the wrapping unit is omitted.

In the examples, the disinfection unit uses ozone and/or another disinfectant for disinfecting and/or sterilizing the instrument. It will be appreciated that the washing unit may also use ozone and/or another disinfectant while washing and/or drying the instrument.

In the examples is referred to dental instruments. It will be appreciated that the to be decontaminated medical instruments can also be instruments or implants for use in other medical fields, such as general medicine, dental medicine, ocular medicine, veterinary medicine, bowel and intestinal medicine, cardio medicine, cardio vascular medicine, oncology medicine, ophthalmology, gynecology, endodontology, etc. The decontamination device can also be used for flash sterilization e.g. in operating rooms. It will be appreciated that the medical instruments to be decontaminated can also be instruments used in a medical environment, such as wearables at a point of care, chairside or bedside. Examples of such wearables are for instance cellphones, beepers, stethoscopes, pens, etc. It will be appreciated that the control unit can be embodied as dedicated electronic circuits, possibly including software code portions. The control unit can also be embodied as software code portions executed on, and e.g. stored in, a memory of, a programmable apparatus such as a computer.

Although the embodiments of the invention described with reference to the drawings comprise computer apparatus and processes performed in computer apparatus, the invention also extends to computer programs, particularly computer programs on or in a carrier, adapted for putting the invention into practice. The program may be in the form of source or object code or in any other form suitable for use in the implementation of the processes according to the invention. The carrier may be any entity or device capable of carrying the program.

For example, the carrier may comprise a storage medium, such as a ROM, for example a CD ROM or a semiconductor ROM, or a magnetic recording medium, for example a floppy disc or hard disk. Further, the carrier may be a transmissible carrier such as an electrical or optical signal which may be conveyed via electrical or optical cable or by radio or other means, e.g. via the internet or cloud.

When a program is embodied in a signal which may be conveyed directly by a cable or other device or means, the carrier may be constituted by such cable or other device or means. Alternatively, the carrier may be an integrated circuit in which the program is embedded, the integrated circuit being adapted for performing, or for use in the performance of, the relevant processes.

However, other modifications, variations, and alternatives are also possible. The specifications, drawings and examples are, accordingly, to be regarded in an illustrative sense rather than in a restrictive sense.

For the purpose of clarity and a concise description features are described herein as part of the same or separate embodiments, however, it will be appreciated that the scope of the invention may include embodiments having combinations of all or some of the features described.

In the claims, any reference signs placed between parentheses shall not be construed as limiting the claim. The word 'comprising' does not exclude the presence of other features or steps than those listed in a claim. Furthermore, the words 'a' and 'an' shall not be construed as limited to 'only one', but instead are used to mean 'at least one', and do not exclude a plurality. The mere fact that certain measures are recited in mutually different claims does not indicate that a combination of these measures cannot be used to an advantage.

The invention claimed is:

1. A method for decontaminating a medical instrument using a decontamination device, the method including:
    loading a to be treated medical instrument into a cassette;
    the method further including:
    loading the cassette into the decontamination device,
    washing and/or drying the instrument in the decontamination device,
    disinfecting and/or sterilizing the instrument in the decontamination device,
    hermetically sealing the cassette containing the disinfected and/or sterilized instrument in the decontamination device; and
    taking the cassette containing the disinfected and/or sterilized instrument out of the decontamination device at consecutive stations within the decontamination device.

2. A method for decontaminating a medical instrument using a decontamination device, the method including:
    loading a to be treated medical instrument into a cassette;
    loading the cassette into the decontamination device;
    washing and/or drying the instrument in the decontamination device;
    disinfecting the instrument in a first cycle and sterilizing the instrument in a second cycle in the decontamination device;
    hermetically sealing the cassette containing the disinfected and sterilized instrument in the decontamination device; and
    taking the cassette containing the disinfected and sterilized instrument out of the decontamination device.

3. The method of claim 1, wherein the washing includes spraying a jet or mist of a cleaning fluid directly onto the instrument.

4. The method of claim 1, including washing the instrument using a liquid containing a disinfectant.

5. The method of claim 1, including spraying a jet or mist of a drying gas directly onto the instrument.

6. The method of claim 1, including washing and/or drying the instrument in the cassette.

7. The method of claim 1, including disinfecting and/or sterilizing the instrument in the cassette.

8. The method of claim 1, wherein the cassette includes a first portion and a second portion that can be closed against each other for enclosing the instrument, the method including hermetically closing the first portion against the second portion.

9. The method of claim 1, including transporting the instrument and/or the cassette through the decontamination device using a transportation unit.

10. The method of claim 1, including providing the instrument and/or the cassette with a label representative of the performed decontamination.

11. The method of claim 1, including, by a control unit, controlling the washing and/or drying, the disinfecting and/or sterilizing and sealing, for automatically washing and/or drying, disinfecting and/or sterilizing and sealing.

12. The method of claim 2, including taking the cassette containing the disinfected and/or sterilized instrument out of the decontamination device at the same location where the cassette was loaded into the decontamination device.

13. The method of claim 2, wherein the cassette includes a first portion and a second portion that can be closed against each other for enclosing the instrument, the method including hermetically closing the first portion against the second portion.

14. The method of claim 2, including providing the instrument and/or the cassette with a label representative of the performed decontamination.

15. A method for decontaminating a medical instrument using a decontamination device, the method including:
loading a to be treated medical instrument into a cassette;
loading the cassette into the decontamination device;
washing and/or drying the instrument in the decontamination device;
disinfecting and/or sterilizing the instrument in the decontamination device;
hermetically sealing the cassette containing the disinfected and/or sterilized instrument in the decontamination device; and
taking the cassette containing the disinfected and/or sterilized instrument out of the decontamination device, the method further including having cassettes of a first type and cassettes of a second type associated with the decontamination device, and applying a first decontamination cycle to cassettes of the first type and a different second cycle to cassettes of the second type.

16. The method of claim 15, including having the decontamination device recognize the type of cassette and automatically select the associated decontamination cycle.

17. A method for decontaminating a medical instrument using a decontamination device, the method including:
loading a to be treated medical instrument into a cassette;
loading the cassette into the decontamination device;
washing the instrument in the decontamination device, wherein the washing includes a first step of ultrasonic washing at 30-40° C., and a second step of spray washing at 40-90° C.;
drying the instrument in the decontamination device;
cooling the instrument in the decontamination device; and
disinfecting and/or sterilizing the instrument in the decontamination device.

18. The method of claim 17, wherein the cooling is performed at 0-30° C. for 10-300 seconds.

19. A method for decontaminating a medical instrument using a decontamination device, the method including:
loading a to be treated medical instrument into a cassette;
loading the cassette into the decontamination device;
washing the instrument in the decontamination device;
drying the instrument in the decontamination device;
cooling the instrument in the decontamination device; and
disinfecting and/or sterilizing the instrument in the decontamination device, wherein the disinfecting and/or sterilizing is performed using a disinfecting/sterilizing agent including recombined ionized humidified air.

20. The method of claim 1, wherein the steps are performed in a consecutive order following one of:
washing, disinfecting and drying;
washing, drying and sterilizing;
washing, disinfecting, drying and sterilizing.

* * * * *